United States Patent [19]

Brown et al.

[11] Patent Number: 4,496,567

[45] Date of Patent: Jan. 29, 1985

[54] PHENYL ALKYLAMINOPYRIMIDONES

[75] Inventors: Thomas H. Brown, Tewin; Robert J. Ife, Stevenage, both of England

[73] Assignee: Smith Kline & French Laboratories Limited, Welwyn Garden City, England

[21] Appl. No.: 91,850

[22] Filed: Nov. 6, 1979

[30] Foreign Application Priority Data

Nov. 13, 1978 [GB] United Kingdom ............... 44260/78
Aug. 21, 1979 [GB] United Kingdom ................. 7929013

[51] Int. Cl.$^3$ ................. A61K 31/505; C07D 239/36; C07D 401/12; C07D 405/12

[52] U.S. Cl. .................................... 514/272; 544/296; 544/321

[58] Field of Search ................. 544/321, 296; 424/251

[56] References Cited

U.S. PATENT DOCUMENTS

| 3,932,644 | 1/1976 | Durant et al. | 424/263 |
| 3,980,781 | 9/1976 | Snell et al. | 424/251 |
| 4,117,131 | 9/1978 | Brown et al. | 544/321 |
| 4,145,546 | 3/1979 | Brown et al. | 544/321 |
| 4,154,834 | 5/1979 | Brown et al. | 544/370 |
| 4,159,329 | 6/1979 | Brown et al. | 544/321 |

FOREIGN PATENT DOCUMENTS

| 867106 | 11/1978 | Belgium . |
| 877889 | 11/1979 | Belgium . |
| 1223686 | 3/1971 | United Kingdom . |

Primary Examiner—Donald G. Daus
Assistant Examiner—James H. Turnipseed
Attorney, Agent, or Firm—Joan S. Keps; Richard D. Foggio; Alan D. Lourie

[57] ABSTRACT

The compounds are phenyl alkylaminopyrimidones which are histamine H$_2$-antagonists. A specific compound of the present invention is 2-[2-[3-(dimethylaminomethyl)benzylthio]ethylamino]-5-(6-methyl-3-pyridylmethyl)-4-pyrimidone.

10 Claims, No Drawings

PHENYL ALKYLAMINOPYRIMIDONES

This invention relates to pharmacologically active compounds, to pharmaceutical compositions containing these compounds and to methods of blocking histamine H$_2$-receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" (histamine H$_1$-receptor antagonists), of which mepyramine, diphenhydramine and chlorpheniramine are typical examples, are mediated through histamine H$_1$-receptors. However, others of the biological actions of histamine are not inhibited by "antihistamines" and actions of this type which are inhibited by burimamide are mediated through receptors which are termed histamine H$_2$-receptors, and which may be defined as those histamine receptors which are not blocked by mepyramine but are blocked by burimamide. Compounds which block histamine H$_2$-receptors are referred to as histamine H$_2$-antagonists.

Blockade of histamine H$_2$-receptors is of utility in inhibiting the biological actions of histamine which are not inhibited by "antihistamines". Histamine H$_2$-antagonists are therefore useful, for example, as inhibitors of gastric acid secretion, as anit-inflammatory agents and as agents which act on the cardiovascular system, for example as inhibitors of the effects of histamine on blood pressure.

In some physiological conditions the biological actions of histamine are mediated through both histamine H$_1$- and H$_2$-receptors and blockade of both types of receptors is useful. These conditions include inflammation mediated by histamine, for example skin inflammation, and those hypersensitivity responses due to the action of histamine at H$_1$- and H$_2$-receptors, for example allergies.

The compounds of this invention have both histamine H$_1$-antagonist and histamine H$_2$-antagonist activity, and are useful in the treatment of conditions wherein histamine H$_2$-antagonists are useful.

The present invention provides compounds of Structure 1

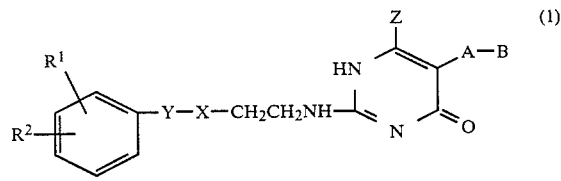

(1)

in which R$^1$ is hydrogen, lower alkyl, lower alkoxy, hydroxy, halogen, trifluoromethyl, nitro, amino, lower alkylamino, lower alkanoylamino, di(lower alkyl)amino or cyano; R$^2$ is in the 3-, 4- or 5-position and is hydrogen, lower alkyl substituted by R$^3$ or ethoxy or propoxy ω-substituted by R$^3$ where R$^3$ is amino, lower alkylamino, di(lower alkyl)-amino, N-piperidino or N-pyrrolidino; Y is methylene or oxygen and X is methylene or sulphur provided that one or two of the groups X and Y is methylene; Z is hydrogen or lower alkyl; A is C$_1$–C$_5$ alkylene or —(CH$_2$)$_p$W—(CH$_2$)$_q$— where W is oxygen or sulphur and p and q are such that their sum is from 1 to 4, and B is hydrogen, methyl, C$_3$–C$_6$ cycloalkyl, a heteroaryl group optionally substituted by one or more (which may be the same or different) of the groups lower alkyl, lower alkoxy, halo, hydroxy and amino, or B is naphthyl, 6-(2,3-dihydro-1,4-benzodioxinyl), a 4- or 5-(1,3-benzodioxolyl) group, or a phenyl group optionally substituted with one or more (which may be the same or different) lower alkyl, lower alkoxy, halogen, aryl(lower alkoxy) (preferably benzyloxy), hydroxy, lower alkoxy-lower alkoxy, trifluoromethyl, di(lower alkyl)amino, phenoxy, halophenoxy, lower alkoxyphenoxy, phenyl, halophenyl or lower alkoxyphenyl groups. The compounds of Structure 1 can be in the form of the free bases or their pharmaceutically acceptable acid addition salts.

Throughout this specification by the terms 'lower alkyl', 'lower alkoxy' and 'lower alkanoyl' are meant alkyl, alkoxy and alkanoyl groups which are straight or branched containing 1 to 4 carbon atoms. Examples of heteroaryl groups are pyridyl, N-oxo-pyridyl, furyl, thienyl, thiazolyl, oxazolyl, isothiazolyl, imidazolyl, pyrimidyl, pyrazyl, pyridazyl, thiadiazolyl, quinolyl, isoquinolyl, 5,6,7-8-tetrahydroquinolyl, benzimidazolyl and benzthiazolyl.

These compounds differ from compounds already disclosed as having histamine H$_2$-antagonist activity in that they do not have a heteroaryl group or an isothioureido group as a feature essential for activity.

Preferably R$^1$ is in the 2- position.

Preferably R$^1$ is hydrogen, lower alkyl, lower alkoxy (particularly methoxy), hydroxy, halogen (particularly chloro), trifluoromethyl, amino or cyano. Particularly preferably R$^1$ is methoxy or chloro when R$^2$ is hydrogen, and R$^1$ is hydrogen when R$^2$ is other than hydrogen.

Preferably R$^2$ is hydrogen or lower alkyl substituted by di(lower alkyl)amino, particularly dimethylaminomethyl.

Preferably when R$^2$ is hydrogen X and Y are both methylene.

Preferably Z is hydrogen.

When B is an optionally substituted phenyl group it is preferably substituted by one or more lower alkoxy groups, and in particular is 3-methoxyphenyl, 4-methoxyphenyl or 3,4-dimethoxyphenyl.

A particular group of compounds is that in which B is a 6-(2,3-dihydro-1,4-benzodioxinyl), 5-(1,3-benzodioxolyl) or 1-naphthyl group.

Where B is a heteroaryl group it is preferably a 2-furyl, 2-thienyl, 2-pyridyl, 3-pyridyl, 4-pyridyl, 2-thiazolyl, 2-imidazolyl, 2-pyrimidyl, 2-pyrazyl, 3-pyridazyl, 3-quinolyl or 1-isoquinolyl group, which group is optionally substituted by one or more lower alkyl or lower alkoxy groups, or a pyridyl or pyrimidyl group substituted by hydroxy, and especially 3-pyridyl, 6-methyl-3-pyridyl, 5,6-dimethyl-3-pyridyl, 6-methoxy-3-pyridyl, 2-methoxy-4-pyridyl, 6-hydroxy-3-pyridyl and 2-hydroxy-4-pyridyl.

Preferably in the compounds of Structure 1 either A is α, ω-straight alkylene and especially methylene (—CH$_2$—), or A is —(CH$_2$)$_p$W(CH$_2$)$_q$— where p is 0, W is oxygen and q is 1 (i.e. A is a —OCH$_2$—, oxymethyl, group). Other examples of A are methoxymethyl, methylthiomethyl, methoxyethyl and methylthioethyl.

The compounds of Structure 1 are shown and described as 4-pyrimidone derivatives and these derivatives exist in equilibrium with the corresponding 6-one tautomers. These compounds also exist to a lesser extent as the hydroxy tautomers, and the pyrimidone ring may also exist in the following tautomeric forms:

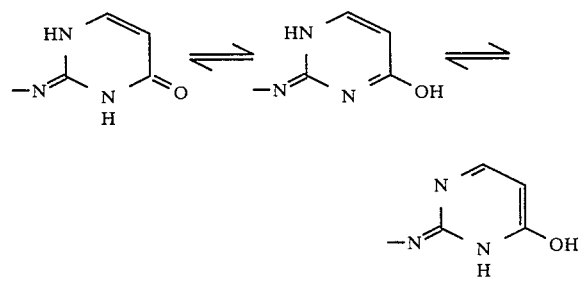

Compounds of Structure 1 in which B is a 3-pyridyl group are preferred because these compounds are in general more active as histamine $H_2$-antagonists than corresponding compounds of Structure 1 in which B is an aryl group when measured after intravenous and oral administration. Compounds of Structure 1 in which B is a 3-pyridyl group with a lower alkyl, lower alkoxy or hydroxy substituent in the 6-position are especially preferred because in general these compounds are at least as effective as $H_2$-antagonists as corresponding compounds in which B is an unsubstituted pyridyl group and the former compounds are less acutely toxic when intravenously administered in high doses to mice.

The compounds of Structure 1 can be prepared by reacting a compound of Structure 3 with an amine of Structure 2, and where necessary removing any amino-protecting group present in the group $R^4$.

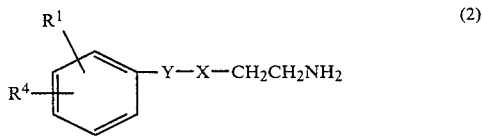

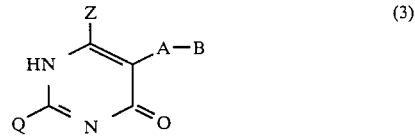

In Structure 2 Y, X and $R^1$ are as defined for Structure 1 and $R^4$ is in the 3-, 4- or 5-position and is hydrogen, lower alkyl substituted by a group $R^5$, or is $R^5CH_2CH_2O-$ or $R^5CH_2CH_2CH_2O-$, where $R^5$ is di(lower alkyl)amino, N-piperidino, N-pyrrolidino, a protected amino group or a protected lower alkylamino group. Examples of amino-protecting groups are t-butoxycarbonyl (removed with trifluoroacetic acid), benzyloxycarbonyl (removed by hydrogenolysis or with hydrogen bromide), or phthaloyl (removed with hydrazine or methylamine). In Structure 3, A, B and Z are as defined for Structure 1 (provided that any hydroxyl groups in B can be optionally protected) and Q is nitroamino ($NO_2NH-$), loweralkylthio, benzylthio, halogen or other grouping which is conveniently displaced by an amine.

Preferably Q is methylthio. Particularly preferably Q is nitroamino.

This reaction can be carried out in the absence of a solvent at an elevated temperature, e.g. 150° C., or in the presence of a solvent, such as in refluxing pyridine. When Q is nitroamino this reaction is preferably carried out in refluxing ethanol, isopropanol or pyridine.

Compounds of Structure 1 in which X is sulphur can also be prepared by reacting a compound of Structure 4

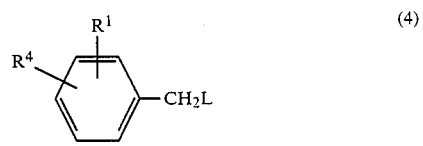

in which $R^1$ and $R^4$ are as defined for Structure 2 and L is a group displaceable with a thiol, for example hydroxy, acyloxy (preferably acetoxy), methanesulphonyloxy or p-toluenesulphonyloxy, lower alkoxy (preferably methoxy), chlorine, bromine or triarylphosphonium (preferably triphenylphosphonium), with a 2-(2-mercaptoethylamino)pyrimidone of Structure 5

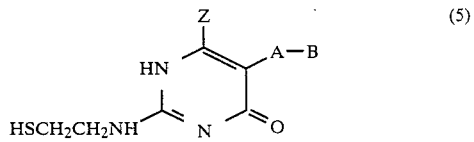

in which Z, A and B are as defined for Structure 1 provided that hydroxy groups in B can be protected, and where necessary removing any protecting groups present. Preferably when L is hydroxy, lower alkoxy or acetoxy the reaction is carried out under acidic conditions, for example in acetic acid or in aqueous hydrochloric or hydrobromic acid. Preferably when L is sulphonyloxy, chlorine, bromine or triarylphosphonium the reaction is carried out in the presence of a base, for example in the presence of sodium ethoxide in ethanol. Preferably L is hydroxy or chlorine.

The compounds of Structure 5 can be prepared by reacting a compound $GSCH_2CH_2NH_2$ where G is hydrogen or a thiol-protecting group, for example trityl, 4-methoxybenyl or $NH_2CH_2CH_2S-$ (in which the thiol is protected as the disulphide) with a pyrimidone of Structure 6

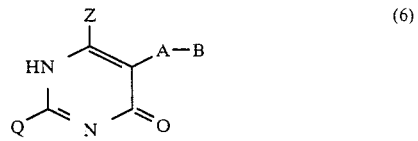

in which Z, A and B are as defined for Structure 1 (provided that hydroxy groups in B can be protected) and Q is nitroamino, lower alkylthio, benzylthio, chlorine or bromine, and removing any thiol-protecting group present.

Hydroxy substituents in the groups B can be protected during these syntheses. Examples of hydroxy protecting groups are methoxymethyl, methylthiomethyl, tetrahydropyranyl, arylmethyl (for example benzyl), lower alkyl (for example methyl) and acyl (for example formyl and acetyl).

Compounds of Structure 1 in which B is N-oxopyridyl and $R^2$ is hydrogen can also be prepared by oxidising the corresponding compounds of Structure 1 in which B is pyridyl, for example using a peroxy acid, for example 3-chloroperoxybenzoic acid.

Compounds of Structure 1 in which B is a 2-, 4- or 6-hydroxypyridyl group can be conveniently prepared by the acid hydrolysis of the corresponding compounds of Structure 1 in which B is a pyridyl group with a 2-, 4- or 6-lower alkoxy substituent.

The amines of Structure 2 in which X is sulphur can be prepared by reacting the appropriate benzyl alcohol with cysteamine in an acidic medium, for example hydrobromic acid or a hydrohalide salt in acetic acid, or by reacting the appropriate benzyl halide (which can be prepared from a benzyl alcohol and a thionyl halide) with cysteamine under basic conditions. Preferably the latter method is used when $R^1$ or $R^2$ is sensitive to treatment with strong acids. These benzyl alcohols can be prepared by reducing the appropriate benzoate ester or benzaldehyde with lithium aluminium hydride or sodium in ethanol, or by converting the appropriately substituted bromobenzene into an aryllithium or arylmagnesium bromide derivative and reacting this with formaldehyde in a solvent, for example tetrahydrofuran. Amines in which $R^1$ is hydroxy can be prepared by cleaving the corresponding amine in which $R^1$ is lower alkoxy, for example by using hydrogen bromide or boron tribromide. Amines in which $R^1$ is amino can be prepared by reducing the corresponding amines in which $R^1$ is nitro.

The amines of Structure 2 in which Y and X are both methylene can be prepared by reacting an aryllithium compound (which can be prepared from an aryl bromide) (a) successively with 1,4-dibromobutane, potassium phthalimide and hydrazine or (b) successively with 4-bromobutylphthalimide and hydrazine, or (c) successively with 1,3-dibromopropane, potassium cyanide and lithium aluminium hydride. The amines of Structure 2 in which Y and X are both methylene, and $R^1$ is nitro, amino, hydroxy, halo, cyano or alkoxy in the 2-position can be prepared by reacting a 2-nitrohalobenzene with 2-(2-cyanoethyl)malonic acid diethyl ester with sodium hydride in tetrahydrofuran, hydrolysing the product to give a 4-(2-nitrophenyl)butyronitrile followed by catalytic reduction to give 4-(2-aminophenyl)butyronitrile, reduction with lithium aluminium hydride to give a 4-(2-aminophenyl)butylamine and conversion into the desired amine by diazotisation at pH 1 and where necessary reaction with a cuprous halide or cuprous cyanide, or by diazotisation in a lower alkanol. The amines in which $R^1$ is 2-lower alkylamino can be prepared by acylating a 4-(2-aminophenyl)butyronitrile and reducing the product.

The amines of Structure 2 in which Y is oxygen can be prepared by two methods:

(i) Reduction of a nitrile of Structure 7

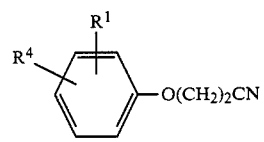

(7)

for example with lithium aluminium hydride or with hydrogen and rhodium on alumina catalyst. The nitriles of Structure 7 can be prepared by reacting the corresponding phenol of Structure 8 with acrylonitrile, (ii) Reaction of a phenol of Structure 8

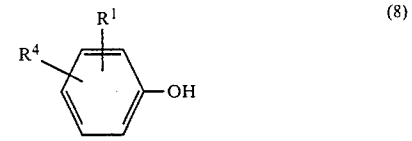

(8)

with N-(3-bromopropyl)phthalimide followed by removal of the phthalimido group with hydrazine or methylamine.

The intermediates of Structure 3 in which Q is nitroamino can be prepared by reacting nitroguanidine with a compound of Structure 9

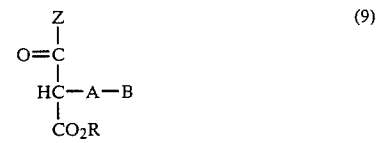

(9)

in which R is lower alkyl, aryl or aralkyl, in the presence of a base. Preferably this reaction is carried out in a lower alkanol with a sodium lower alkoxide as the base, and preferably at the boiling point of the reaction mixture.

This invention includes the obvious chemical equivalents of the compounds of Structure 1, for example, those compounds with additional substituents on the benzene ring which do not substantially affect the essential utility possessed by the compounds of Structure 1.

The compounds of Structure 1 block histamine $H_2$-receptors, that is they inhibit the biological actions of histamine which are not inhibited by "antihistamines" such as mepyramine but are inhibited by burimamide. For example, the compounds of this invention inhibit histamine-stimulated secretion of gastric acid from the lumen-perfused stomachs of rats anaesthetised with urethane, at doses of less than 32 micromoles per kilogram intravenously. This procedure is referred to in Ash and Schild, Brit.J.Pharmac.Chemother., 27, 427, (1966). The specific compounds of Structure 1 described in Examples 7, 8, 9 and 14 inhibit histamine-stimulated gastric acid secretion by 50% after intravenous doses of less than 1 micromole per kilogram. The activity of these compounds as histamine $H_2$-antagonists is also demonstrated by their ability to inhibit other actions of histamine which, according to the above mentioned paper of Ash and Schild, are not mediated by histamine $H_1$-receptors. For example, the specific compounds described in the Examples 1 to 14 inhibit the actions of histamine on the isolated guinea pig atrium and isolated rat uterus at doses of less than $0.5 \times 10^{-5}$ Molar. The compounds of Structure 1 in which $R^2$ is a substituted lower alkyl group are significantly more active as $H_2$-antagonists than corresponding compounds in which $R^2$ is hydrogen.

The compounds of this invention inhibit the basal secretion of gastric acid and also that stimulated by pentagastrin or by food.

In addition, in a conventional test, such as the measurement of blood pressure in the anaesthetized rat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat and the dose producing 50% inhibition of histamine-induced tachycardia in the isolated guinea pig atrium.

The compounds of Structure 1 also block histamine $H_1$-receptors, that is they inhibit the biological actions of histamine which are inhibited by mepyramine, diphenhydramine and chlorpheniramine. For example the specific compounds described in the Examples inhibit the action of histamine in the isolated guinea pig ileum at doses of about $10^{-4}$ Molar and Examples in which $R^2$ is hydrogen inhibit at $10^{-6}$ Molar.

The pharmaceutical compositions of the invention comprise a pharmaceutical carrier and a pharmacologically active compound of Structure 1 which can be in the base form or in the form of an addition salt with a pharmaceutically-acceptable acid. Such addition salts include those with hydrochloric, hydrobromic, hydriodic, sulphuric and maleic acids and may conveniently be formed from the corresponding compounds of Structure 1 by standard procedures, for example by treating them with an acid in a lower alkanol or by the use of ion exchange resins to form the required salt either directly from the compound in the base form from a different addition salt.

The pharmaceutical carrier employed can be a solid or liquid. Examples of solid carriers are lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

If a solid carrier is used, the composition can be prepared in the form of a tablet, capsule containing powder or pellets, troche or lozenge. The amount of solid carrier in a unit dosage form is generally from about 25 mg of about 300 mg. If a liquid carrier is used, the preparation may be in the form of a syrup, emulsion, sterile injectable liquid or an aqueous or nonaqueous solution or liquid suspension. Other additives such as preservatives, e.g. antioxidants or antibacterials and/or flavouring or colouring agents may also be included. The liquid forms can be prepared in soft gelatin capsules or microcapsules. The sterile solution can be prepared in ampoules, multidose vials or unit dose disposable syringes. The preparation can also be in a semi-solid form such as a cream, paste, ointment or gel or a liquid or aerosol form for topical administration.

The pharmaceutical compositions are prepared by conventional techniques involving procedures such as mixing, granulating and compressing or dissolving the ingredients as appropriate to the desired preparation.

The active ingredient is present in the compositions in an effective amount to block histamine $H_2$-receptors. The route of administration can be oral, by intravenous injection or infusion, rectal or topical.

Preferably, each dosage unit contains the active ingredient in an amount of from about 60 mg to about 250 mg.

A method of blocking histamine $H_2$-receptors by administering to an animal a compound of Structure 1 is also an object of this invention. Also, this invention includes a method of simultaneously blocking histamine $H_1$-receptors and histamine $H_2$-receptors by administering to an animal a compound of Structure 1.

The active ingredient is preferably administered one to six times per day. The daily dosage regimen is preferably from about 150 mg to about 1500 mg.

Advantageously the composition is made up in a dosage form appropriate to the desired mode of administration, for example, as a tablet, capsule, injectable solution or as a cream or ointment for topical application, or as a suppository or enema for rectal administration.

The invention is illustrated but in no way limited by the following Examples, in which temperatures are in degrees Centigrade.

EXAMPLE 1

(i) Cysteamine hydrochloride (2.12 g) was added to a solution of sodium ethoxide (from 0.87 g sodium) in ethanol (50 ml) stirred under nitrogen in an ice-bath. 2-Methoxybenzyl chloride (2.93 g) was added dropwise and the mixture was stirred in an ice-bath for 0.5 hr. and allowed to stand at room temperature overnight. The mixture was evaporated to dryness. Water was added to the residue and the mixture was extracted at pH 3 with chloroform (discarded), adjusted to pH 13 and extracted a second time with chloroform. This second extract was purified by elution from silica gel with chloroform/methanolic ammonia (50:1) to give 2-(2-methoxybenzylthio)ethylamine (1.35 g) as an oil which was treated with hydrogen chloride in ethanol to give the hydrochloride m.p. 128°–30° (ethanol/ether).

(ii) 2-(2-Methoxybenzylthio)ethylamine (1.18 g) and 2-methylthio-5-(3-pyridylmethyl)-4-pyrimidone (1.0 g) were fused together at 170° for 50 minutes and allowed to cool. Water was added and the mixture was extracted at pH 13 with chloroform (discarded), adjusted to pH 7 and extracted a second time with chloroform. The second extract was evaporated to give 2-[2-(2-methoxybenzylthio)-ethylamino]-5-(3-pyridylmethyl)-4-pyrimidone as an oil which was treated with hydrogen chloride in ethanol and recrystallised from ethanol-ether to give the dihydrochloride m.p. 180°–183°.

EXAMPLE 2

A mixture of 4-phenylbutylamine (4.0 g), 2-methylthio-5-(3-pyridylmethyl)-4-pyrimidone (5.8 g) and dry pyridine (40 ml) was heated under reflux for 60 hours and evaporated to dryness. Water was added to the residue and the pH was adjusted to 7 with hydrochloric acid. The solid which separated out was recrystallised from aqueous ethanol to give 2-(4-phenylbutylamino)-5-(3-pyridylmethyl)-4-pyrimidone dihydrate m.p. about 70°.

EXAMPLE 3

A mixture of 4-phenylbutylamine (1.12 g), 5-[5-(1,3-benzodioxolylmethyl)]-2-methylthio-4-pyrimidone (1.38 g) and dry pyridine (15 ml) was heated under reflux for 50 hours and evaporated to dryness. The residue was twice recrystallised from ethanol to give 2-(4-phenylbutylamino)-5-[5-(1,3-benzodioxolylmethyl)]-4-pyrimidone (1.26 g) m.p. 158°–159°.

EXAMPLE 4

A mixture of 5-(3-pyridylmethyl)-2-methylthio-4-pyrimidone (1.0 g), 2-(benzylthio)ethylamine (1.06 g) and dry pyridine (30 ml) was heated under reflux for 40 hours and evaporated to dryness. Water was added to the residue and the mixture was extracted with chloroform (discarded). The aqueous phase was adjusted to pH 7 and was extracted with chloroform. This extract was evaporated to dryness and the residue was recrystallised from ethanol to give 2-[2-benzylthio)e- thylamino]-5-(3-pyridylmethyl)-4-pyrimidone m.p. 145°-148°.

EXAMPLE 5

(i) A mixture of 6-methylpyridine-3-carboxaldehyde (51.57 g). malonic acid (44.30 g), piperidine (6 ml) and pyridine (300 ml) was stirred at 100° for 3 hours and was allowed to cool. The mixture was evaporated to dryness, water was added to the residue and the solid was filtered off and recrystallised from ethanol-acetic acid to give 3-(6-methyl-3-pyridyl)acrylic acid (41.25 g) m.p. 213.5°-215°.

(ii) A stirred mixture of 3-(6-methyl-3-pyridyl)acrylic acid (50.70 g) dry ethanol (350 ml) and concentrated sulphuric acid (25 ml) was heated under reflux for 18 hours and ethanol (~250 ml) was removed by evaporation. The residue was poured into ice-aqueous ammonia and the mixture was extracted with ether. The ether extracts were washed with water and evaporated to an oil which crystallised on standing to give ethyl 3-(6-methyl-3-pyridyl)-acrylate m.p. 36°-37°.

(iii) Ethyl 3-(6-methyl-3-pyridyl)acrylate (60.36 g) was hydrogenated in ethanol at 35° and 344 kPa using palladium-on-charcoal catalyst (10%, 1.0 g). The mixture was filtered and the filtrate was evaporated to give ethyl 3-(6-methyl-3-pyridyl)propionate as an oil.

(iv) Ethyl 3-(6-methyl-3-pyridyl)propionate (57.79 g) and ethyl formate (23.71 g) were added over 2.5 hours to a stirred mixture of sodium wire (6.88 g) and ether (200 ml) cooled in an ice-salt bath. The mixture was stirred for 20 hours and the ether was removed by evaporation. Thiourea (22.76 g) and ethanol (175 ml) was added to the residue and the mixture was heated under reflux for 7 hours and evaporated to dryness. Water (200 ml) was added to the residue and the mixture was adjusted to pH 6 with acetic acid. The solid was filtered off and recrystallised from methanol/acetic acid to give 5-(6-methyl-3-pyridylmethyl)-2-thiouracil (17.24 g) m.p. 240°-241°.

(v) Methyl iodide (13.79 g) was added to a stirred solution of 5-(6-methyl-3-pyridylmethyl)-2-thiouracil (22.66 g) and sodium hydroxide (8.0 g) in water (250 ml) and ethanol (250 ml), and the mixture was heated at 70° for 1 hour and stirred at room temperature overnight. Acetic acid was added to pH 5 and the volume of the mixture was evaporated to a volume of 50 ml. The solid was filtered off and was recrystallised from ethanol-acetic acid to give 5-(6-methyl-3-pyridylmethyl)-2-methylthio-4-pyrimidone (10.16 g) m.p. 197°-197.5°.

(vi) A mixture of 4-phenylbutylamine (2.7 g), 5-(6-methyl-3-pyridylmethyl)-2-methylthio-4-pyrimidone (3.0 g) and dry pyridine (20 ml) was heated under reflux for 40 hours, and evaporated to dryness. Water was added to the residue and the pH of the mixture was adjusted to 7. The solid was filtered off and was recrystallized from aqueous ethanol to give 2-(4-phenylbutylamino)-5-(6-methyl-3-pyridylmethyl)-4-pyrimidone hydrate m.p. 151°-152°.

EXAMPLE 6

A solution of 3-chloroperoxybenzoic acid (1.5 g) in chloroform (15 ml) was added dropwise to a stirred solution of 2-(4-phenylbutylamino)-5-(6-methyl-3-pyridylmethyl)-4-pyrimidone (2.44 g) in chloroform (15 ml) maintained at 20°. The mixture was stirred for a further 3 hours at room temperature and was repeatedly extracted with 0.1N aqueous sodium hydroxide. The chloroform phase was washed with water, evaporated to dryness and the residue was recrystallised from acetonitrile/methanol to give 2-(4-phenylbutylamino)-5-(N-oxo-6-methyl-3-pyridylmethyl)-4-pyrimidone (1.25 g) m.p. 117°-125°.

EXAMPLE 7

(i) Dimethylamine (51.4 g, 1.14 mol) was reacted with 3-bromobenzyl bromide (95 g, 0.38 mol) in benzene at 5° and the mixtue was acidified with hydrochloric acid and the mixture was extracted with aqueous 3N hydrochloric acid. The aqueous extracts were made alkaline with aqueous potassium hydroxide and the oil which separated out was distilled to give 3-bromo-N,N-dimethylbenzylamine (65 g, 80%) b.p. 118°/20 mmHg.

(ii) 3-Bromo-N,N-dimethylbenzylamine (21.4 g) was reacted with magnesium turnings (2.4 g) in dry tetrahydrofuran (75 ml). The mixture was cooled to 0° and gaseous formaldehyde (generated by heating 15 g paraformaldehyde in a stream of argon) was passed over the stirred solution. Tetrahydrofuran (25 ml) was added and the mixture was stirred at room temperature for 2.5 hours and acidified to pH 1. The mixture was extracted with aqueous 3N hydrochloric acid, and the aqueous extracts were made alkaline with aqueous sodium hydroxide and extracted with ether. The ether extracts were evaporated to give 3-(dimethylaminomethyl)benzyl alcohol (14.78 g, 78%).

(iii) Equimolar quantities of 3-(dimethylaminomethyl)benzyl alcohol and cysteamine hydrochloride were heated under reflux for 5 hours in 12N aqueous hydrochloric acid and the mixture was evaporated to give 2-[3-(dimethylaminomethyl)benzylthio]ethylamine dihydrochloride.

(iv) 2-[3-(Dimethylaminomethyl)benzylthio]ethylamine dihydrochloride (4.2 g) was dissolved in water and the solution was made alkaline with aqueous sodium hydroxide and extracted with chloroform. The chloroform extract was evaporated to give the free base. 2-Nitroamino-5-(3-pyridylmethyl)-4-pyrimidone (3.16 g) was added to the residue and the mixture was heated under reflux in ethanol (20 ml) for 35 hours and evaporated to dryness. Water (30 ml) was added to the residue and the mixture was adjusted to pH 13 with aqueous sodium hydroxide and extracted with chloroform. The latter chloroform extracts were evaporated and the residue was recrystallised from acetonitrile to give 2-[2-(3-(dimethylaminomethyl)-benzylthio)ethylamino]-5-(3-pyridylmethyl)-4-pyrimidone m.p. 143°-145°. Treatment with hydrogen chloride in ethanol gives the trihydrochloride salt and treatment with hydrogen bromide in ethanol gives the trihydrobromide salt.

This product can be similarly prepared from 2-methylthio-5-(3-pyridylmethyl)-4-pyrimidone.

2-Nitroamino-5-(3-pyridylmethyl)-4-pyrimidone can be prepared by the following procedure:

Sodium (1.15 g) was dissolved in methanol (50 ml) and nitroguanidine (4.7 g) was added to the cooled solution. The mixture was heated under reflux for 45 minutes, ethyl 2-formyl-3-(3-pyridyl)propionate (9.3 g) was added portionwise and the mixture was heated under reflux for 45 hours and evaporated to dryness. Water was added to the residue and the mixture was extracted with chloroform. The residual aqueous phase was adjusted to pH 5 with acetic acid, and the solid which precipitated was filtered off, washed and dried to give 2-nitroamino-5-(3-pyridylmethyl)-4-pyrimidone, m.p. 214.5°-216°, in 38% yield.

EXAMPLE 8

(i) Reaction of dimethylamine with 4-bromobenzyl bromide in cold benzene gave 4-bromo-N,N-dimethylbenzylamine which was successively reacted with magnesium, formaldehyde, and cysteamine (in a similar procedure to Example 7) to give 2-[4-(dimethylaminomethyl)benzylthio]ethylamine as an oil.

(ii) Reaction of 2-[4-(dimethylaminomethyl)benzylthio]-ethylamine (1.7 g) with 2-nitroamino-5-(3-pyridylmethyl)-4-pyrimidone (1.7 g) in a similar manner to Example 7(iv) gave 2-[2-(4-(dimethylaminomethyl)benzylthio)ethylamino]-5-(3-pyridylmethyl)-4-pyrimidone m.p. 127°–130°. A sample recrystallised a further time from acetonitrile had m.p. 124°–126°.

EXAMPLE 9

(i) A solution of ethyl 2-formyl-3-[5-(1,3-benzodioxolyl)]-propionate (7.5 g) in methanol (20 ml) was added to sodium methoxide in methanol (prepared from 0.689 g sodium and 50 ml methanol); nitroguanidine (3.12 g) was then added to the stirred mixture. The mixture was heated under reflux for 18 hours and evaporated to a residue which was dissolved in water (200 ml) and the solution was extracted with chloroform. The residual aqueous phase was adjusted to pH 5 with acetic acid and the while solid which precipitated was filtered off to give 2-nitroamino-5-[5-(1,3-benzodioxolyl)methyl]-4-pyrimidone (4.08 g), m.p. 200°–2°. A sample recrystallised from aqueous acetic acid had m.p 201.5°–2.5°.

(ii) A mixture of 2-[3-(dimethylaminomethyl)-benzylthio]ethylamine (1.59 g), 2-nitroamino-5-[5-(1,3-benzodioxolyl)methyl]-4-pyrimidone (1.87 g) and pyridine (8 ml) was heated under reflux for 3 hours, evaporated to dryness and the residue was heated at 160°–170° for 2 hours. The cooled residue was suspended in chloroform and extracted with 0.1N hydrochloric acid to remove the unreacted amine and subsequently with 1.0N hydrochloric acid to extract the required product, and the latter acid extracts were evaporated to dryness and recrystallised from ethanol containing hydrogen chloride to give 2-[2-(3-dimethylaminomethyl)-benzylthio)ethylamino]-5-[5-(1,3-benzodioxolyl)methyl]-4-pyrimidone dihydrochloride m.p. 176°–178°.

This product can be prepared in a similar manner from 2-methylthio-5-[5-(1,3-benzodioxolyl)methyl]-4-pyrimidone.

EXAMPLE 10

(i) Reaction of 3-bromo-4-methoxybenzyl chloride with dimethylamine in cold benzene gave 3-bromo-4-methoxy-N,N-dimethylamine, b.p. 124°–126°/1.2 mm Hg.

(ii) Successive reaction of 3-bromo-4-methoxy-N,N-dimethylbenzylamine with magnesium and formaldehyde (in a similar manner to Example 7) gave 5-dimethylaminomethyl-2-methoxybenzyl alcohol, m.p. 67°–69°, which was heated under reflux for 4 hours with cysteamine hydrochloride in acetic acid to give, after basification and chloroform extraction, 2-(5-dimethylaminomethyl-2-methoxybenzylthio)ethylamine, as an oil. This oil was heated under reflux with 1.1 molar equivalents of 2-nitroamino-5-(3-pyridylmethyl)-4-pyrimidone in ethanol for 28 hours to give 2-[2-(5-dimethylaminomethyl-2-methoxybenzylthio)-ethylamino]-5-(3-pyridylmethyl)-4-pyrimidone which was treated with hydrogen chloride in ethanol and purified as the trihydrochloride salt m.p. 232°–235° (recrystallised from methanol-ethanol).

EXAMPLE 11

A mixture of 2-(5-dimethylaminomethyl-2-methoxybenzylthio)ethylamine (1.6 g) and 2-nitroamino-5-[5-(1,3-benzodioxolyl)methyl]-4-pyrimidone (1.66 g) was dissolved in pyridine and the mixture was evaporated to dryness and heated at 160°–170° for 2 hours. The cooled mixture was purified chromatographically eluting a silica column with chloroform-methanol (20:1) to give 2-[2-(5-dimethylaminomethyl-2-methoxybenzylthio)ethylamino]-5-[5-(1,3-benzodioxolyl)methyl]-4-pyrimidone which was treated with hydrogen chloride in ethanol and purified as the dihydrochloride salt, m.p. 122°–125° (recrystallised from ethanol/2-propanol).

EXAMPLE 12

A mixture of 2-nitroamino-5-(3-pyridylmethyl)-4-pyrimidone (2.08 g), 3-[3-dimethylaminomethyl)phenoxy]propylamine (1.85 g, 1.05 equiv) and dry pyridine (5 ml) was heated under reflux for 18 hours and evaporated to dryness. Water was added to the residue and the mixture was extracted with chloroform. The chloroform extract was evaporated and the residue recrystallised from acetonitrile to give 2-[3-(3-(dimethylaminomethyl)phenoxy)propylamino]-5-(3-pyridylmethyl)-4-pyrimidone m.p. 103°–104°.

This compound can also be made in a similar manner from 2-methylthio-5-(3-pyridylmethyl)-4-pyrimidone.

EXAMPLE 13

A mixture of 2-nitroamino-5-[5-(1,3-benzodioxolyl)-methyl]-4-pyrimidone (2.9 g), 3-[3-(dimethylaminomethyl)phenoxy]propylamine (3.0 g, 1.5 equiv) and pyridine (5 ml) was heated under reflux for 20 hours and evaporated to dryness. The residue was dissolved in 2N aqueous hydrochloric acid and was extracted with diethyl ether; the aqueous phase was adjusted to pH 14 with 40% w/w aqueous sodium hydroxide and extracted with chloroform. The chloroform extract was evaporated to give 2-[3-(3-(dimethylaminomethylphenoxy)propylamino]-5-[5-(1,3-benzodioxolyl)methyl]-4-pyrimidone m.p. 75°–76° which was treated with hydrogen chloride in ethanol and isolated as the dihydrochloride salt m.p. 158°–160° (hygroscopic).

In a similar manner 2-[3-(3-(dimethylaminomethylphenoxy)propylamino]-5-[6-methyl-3-pyridylmethyl]-4-pyrimidone m.p. 136°–137° (acetonitrile) was prepared from 2-nitroamino-5-(6-methyl-3-pyridylmethyl)-4-pyrimidone.

EXAMPLE 14

A mixture of 2-nitroamino-5-(6-methyl-3-pyridylmethyl)-4-pyrimidone (1.0 g),2-[3-(dimethylaminomethyl)-benzylthio]ethylamine (1.30 g, 1.5 equivalents) and ethanol (3 ml) was heated under reflux for 29 hours and evaporated to dryness. The residue was dissolved in water and the solution was adjusted to pH13 and extracted with ether (which was discarded). The aqueous phase was adjusted to pH 10.5 with hydrochloric acid and the solution was extracted with ether and chloroform. The combined organic extracts were evaporated to dryness and the residue was crystallised from acetonitrile to give 2-[2-[3-(dimethylaminomethyl)benzylthio]ethylamino]-5-(6-methyl-3-pyridylmethyl)-4-pyrimidone m.p. 122°–125°. Treatment with hydrogen chloride in ethanol gives the trihydrochloride salt and treatment with hydrogen bromide in ethanol gives the trihydrobromide salt.

EXAMPLE 15

Reaction of 2-(3-dimethylaminomethylbenzylthio)ethylamine by heating under reflux for 40 hours in dry pyridine with 5-(3-methoxybenzyl)-2-methylthio-4-pyrimidone gives 2-[2-(3-dimethylaminomethylbenzylthio)ethylamino]-5-(3-methoxybenzyl)-4-pyrimidone.

EXAMPLE 16

2-Methoxy-5-(diethylaminomethyl)benzyl alcohol (British Patent Specification No. 594624) is treated with thionyl chloride to give the benzyl chloride and this is reacted with cysteamine and sodium ethoxide in ethanol to give 2-(2-methoxy-5-(diethylaminomethyl)benzylthio)ethylamine. This amine is heated under reflux for 40 hours in dry pyridine with 5-(6-methyl-3-pyridylmethyl)-2-methylthio-4-pyrimidone to give 2-[2-(2-methoxy-5-(diethylaminomethyl)benzylthio)ethylamino]-5-(6-methyl-3-pyridylmethyl)-4-pyrimidone.

EXAMPLE 17

Reaction of equimolar amounts of 2-[3-(dimethylaminomethyl)benzylthio]ethylamine and
(i)  2-nitroamino-5-(6-methoxy-3-pyridylmethyl)-4-pyrimidone
(ii)  2-nitroamino-5-(2-methoxy-4-pyridylmethyl)-4-pyrimidone by heating under reflux in ethanol for 24 hours gives
(a)  2-[2-(3-(dimethylaminomethyl)benzylthio)ethylamino]-5-(6-methoxy-3-pyridylmethyl)-4-pyrimidone
(b)  2-[2-(3-(dimethylaminomethyl)benzylthio)ethylamino]-5-(2-methoxy-4-pyridylmethyl)-4-pyrimidone which give
(c)  2-[2-(3-(dimethylaminomethyl)benzylthio)ethylamino]-5-(6-hydroxy-3-pyridylmethyl)-4-pyrimidone
(d)  2-[2-(3-(dimethylaminomethyl)benzylthio)ethylamino]-5-(2-hydroxy-4-pyridylmethyl)-4-pyrimidone
when heated under reflux with 2N hydrochloric acid in ethanol.

EXAMPLE 18

Reaction of 2-[3-(dimethylaminomethyl)benzylthio]ethylamine with 2-nitroamino-5-(4-methoxy-2-pyridylmethyl)-4-pyrimidone in refluxing ethanol gives 2-[2-(3-(dimethylaminomethyl)benzylthio)ethylamino]-5-(4-methoxy-2-pyridylmethyl)-4-pyrimidone which when reacted with boron tribromide gives 2-[2-(3-(dimethylaminomethyl)benzylthio)ethylamino]-5(4-hydroxy-2-pyridylmethyl)-4-pyrimidone.

EXAMPLE 19

Reaction of 2-[3-(dimethylaminomethyl)benzylthio]ethylamine with an equimolar amount of 2-nitroamino-5-(5,6-dimethyl-3-pyridylmethyl)-4-pyrimidone by heating under reflux in ethanol for 48 hours gives 2-[2-(3-(dimethylaminomethyl)benzylthio)ethylamino]-5-(5,6-dimethyl-3-pyridylmethyl)-4-pyrimidone.

EXAMPLE 20

(i) 3-(2-(Dimethylamino)ethoxy)anisole is reacted with boron tribromide to give 3-(2-(dimethylamino)ethoxy)phenol which is reacted with sodium hydride and N-(3-bromopropyl)phthalimide and the product deprotected with methylamine to give 3-(3-(2-(dimethylamino)ethoxy)phenoxy)propylamine.

(ii) Equimolar amounts of 3-(3-(2-(dimethylamino)ethoxy)phenoxy)propylamine and 2 -nitroamino-5-(6-methyl-3-pyridylmethyl)-4-pyrimidone are heated under reflux in dry pyridine for 24 hours to give 2-[3-(3-(2-dimethylaminoethoxy)phenoxy)propylamino]-5-(6-methyl-3-pyridylmethyl)-4-pyrimidone.

EXAMPLE 21

Reaction of
(i) 3-[4-(dimethylaminomethyl)phenoxy]propylamine
(ii) 3-[3-(1-pyrrolidinylmethyl)phenoxy]propylamine
(iii) 3-[3-(2-dimethylaminoethyl)phenoxy]propylamine
(iv)  3-[3-(3-dimethylaminopropyl)phenoxy]propylamine
(v) 3-[3-(methylaminomethyl)phenoxy]propylamine
(vi) 2-[3-(methylaminomethyl)benzylthio]ethylamine
(vii) 2-[4-(dimethylaminomethyl)benzylthio]ethylamine
(viii) 4-[3-(dimethylaminomethyl)phenyl]butylamine
with 2-nitroamino-5-(6-methyl-3-pyridylmethyl)-4-pyrimidone by heating under reflux in pyridine gives:
(a)  2-[3-(4-(dimethylaminomethyl)phenoxy)propylamino]-5-(6-methyl-3-pyridylmethyl)-4-pyrimidone
(b)  2-[3-(3-(1-pyrrolidinylmethyl)phenoxy)propylamino]-5-(6-methyl-3pyridylmethyl)-4-pyrimidone
(c)  2-[3-(3-(2-dimethylaminoethyl)phenoxy)propylamino]-5-(6-methyl-3-pyridylmethyl)-4-pyrimidone
(d)  2-[3-(3-(3-dimethylaminopropyl)phenoxy)propylamino]-5-(6-methyl-3-pyridylmethyl)-4-pyrimidone
(e)  2-[3-(3-(methylaminomethyl)phenoxy)propylamino]-5-(6-methyl-3-pyridylmethyl)-4-pyrimidone
(f)  2-[2-(3-(methylaminomethyl)benzylthio)ethylamino]-5-(6-methyl-3-pyridylmethyl)-4-pyrimidone
(g)  2-[2-(4-(dimethylaminomethyl)benzylthio)ethylamino]-5-(6-methyl-3-pyridylmethyl)-4-pyrimidone
(h) 2-[4-(3-(dimethylaminomethyl)phenyl)butylamino]-5-(6-methyl-3-pyridylmethyl)-4-pyrimidone

EXAMPLE 22

Reaction of
(a) 5-(2-pyridylmethyl)-2-methylthio-4-pyrimidone
(b) 5-(4-pyridylmethyl)-2-methylthio-4-pyrimidone
(c) 5-(2-thienylmethyl)-2-methylthio-4-pyrimidone
(d) 5-(4-methylbenzyl)-2-methylthio-4-pyrimidone
(e) 5-(3,4,5-trimethoxybenzyl)-2-methylthio-4-pyrimidone
(f) 5-(4-chlorobenzyl)-2-methylthio-4-pyrimidone
(g) 5-(2-chlorobenzyl)-2-methylthio-4-pyrimidone
(h) 5-(3,4-dichlorobenzyl)-2-methylthio-4-pyrimidone
with one equivalent of 2-[3-(dimethylaminomethyl)benzylthio]ethylamine by boiling under reflux in pyridine for 24 hours gives
(a)  2-[2-(3-dimethylaminomethyl)benzylthio)ethylamino]-5-(2-pyridylmethyl)-4-pyrimidone
(b)  2-[2-(3-(dimethylaminomethyl)benzylthio)ethylamino]-5-(4-pyridylmethyl)-4-pyrimidone
(c)  2-[2-(3-dimethylaminomethyl)benzylthio)ethylamino]-5-(2-thienylmethyl)-4-pyrimidone (d) 2-[2-(3-(dimethylaminomethyl)benzylthio)ethylamino]-5-(4-methylbenzyl)-4-pyrimidone
(e) 2-[2-(3-(dimethylaminomethyl)benzylthio)ethylamino]-5-(3,4,5-trimethoxybenzyl)-4-pyrimidone
(f) 2-[2-(3-(dimethylaminomethyl)benzylthio)ethylamino]-5-(4-chlorobenzyl)-4-pyrimidone
(g) 2-[2-(3-(dimethylaminoethyl)benzylthio)ethylamino]-5-(2-chlorobenzyl)-4-pyrimidone
(h) 2-[2-(3-(dimethylaminomethyl)benzylthio)ethylamino]-5-(3,4-dichlorobenzyl)-4-pyrimidone.

Substitution of 3-(3-(dimethylaminomethyl)phenoxy)propylamine gives the corresponding 2-[3-(3-(dimethylaminomethyl)phenoxy)propylamino]pyrimidones.

EXAMPLE 23

Reaction of
(a) 5-benzyloxy-2-methylthio-4-pyrimidone
(b) 5-(2-(4-methoxybenzyloxy)ethyl)-2-methylthio-4-pyrimidone
(c) 5-(2-(4-methoxybenzylthio)ethyl)-2-methylthio-4-pyrimidone
(d) 5-(2-(3-pyridylmethylthio)ethyl)-2-methylthio-4-pyrimidone
(e) 5-(2-phenylethyl)-2-methylthio-4-pyrimidone
(f) 5-(2-phenylethyl)-6-methyl-2-methylthio-4-pyrimidone
(g) 5-(2-phenylbutyl)-2-methylthio-4-pyrimidone with one equivalent of 2-[3-(dimethylaminomethyl)benzylthio]ethylamine by boiling under reflux in pyridine for 24 hours gives (a) 2-[2-(3-(dimethylaminomethyl)benzylthio)ethylamino]-5-benzyloxy-4-pyrimidone
(b) 2-[2-(3-(dimethylaminomethyl)benzylthio)ethylamino]-5-(2-(4-methoxybenzyloxy)ethyl)-4-pyrimidone
(c) 2-[2-(3-(dimethylaminomethyl)benzylthio)ethylamino]-5-(2-(4-methoxybenzylthio)ethyl)-4-pyrimidone
(d) 2-[2-(3-(dimethylaminomethyl)benzylthio)ethylamino]-5-(2-(3-pyridylmethylthio)ethyl)-4-pyrimidone
(e) 2-[2-(3-(dimethylaminomethyl)benzylthio)ethylamino]-5-(2-phenylethyl)-4-pyrimidone
(f) 2-[2-(3-(dimethylaminomethyl)benzylthio)ethylamino]-5-(2-phenylethyl)-6-methyl-4-pyrimidone
(g) 2-[2-(3-(dimethylaminomethyl)benzylthio)ethylamino]-5-(4-phenylbutyl)-4-pyrimidone Substitution of 3-(3-(dimethylaminomethyl)phenoxy)propylamine gives the corresponding 2-[3-(3-(dimethylaminomethyl)phenoxy)propylamino]pyrimidones.

EXAMPLE 24

Substitution of the following 3-(heteroaryl)propionates:
(a) ethyl 3-(2-methoxy-3-pyridyl)propionate
(b) ethyl 3-(4,6-dimethoxy-3-pyridyl)propionate
(c) ethyl 3-(2,6-dimethoxy-4-pyridyl)propionate
(d) ethyl 3-(4,5-dimethoxy-2-pyridyl)propionate
(e) ethyl 3-(5-hydroxy-2-pyridyl)propionate
(f) ethyl 3-(4-hydroxy-2-pyrimidyl)propionate
(g) ethyl 3-(4-hydroxy-5-methoxy-2-pyridyl)propionate
(h) ethyl 3-(4-hydroxy-3-methoxy-2-pyridyl)propionate
(i) ethyl 3-(4,5-dimethyl-2-thienyl)propionate
(j) ethyl 3-(6-amino-3-pyridyl)propionate
(k) ethyl 3-(4-isoquinolyl)propionate
(l) ethyl 3-(3-chloro-2-pyridyl)propionate for ethyl 3-(3-pyridyl)propionate in the procedure of Example 5(iv)–(v) and fusion of the resultant 2-methylthio-4-pyrimidones with 2-[3-(dimethylaminomethyl)benzylthio]ethylamine gives the corresponding 2-[2-(3-(dimethylaminomethyl)-benzylthio)ethylamino]-5-heteroarylmethyl-4-pyrimidones.

The starting materials may be prepared by condensing the corresponding heterocyclic carboxaldehyde with (i) malonic acid, and hydrogenating and esterifying the products or (ii) diethyl malonate, reducing the product with sodium borohydride followed by hydrolysis, monodecarboxylation and esterification, or by reacting a halomethylheterocyclic derivative with sodium and diethyl malonate, and hydrolysing, monodecarboxylating and esterifying the product.

EXAMPLE 25

Substitution of the following 3-arylpropionates:
(a) ethyl 3-(6-(2,3-dihydro-1,4-benzodioxinyl))propionate
(b) ethyl 3-(3-benzyloxyphenyl)propionate
(c) ethyl 3-(3-methoxymethoxyphenyl)propionate (prepared by reacting ethyl 3-(3-hydroxyphenyl)propionate with dimethoxymethane)
(d) ethyl 3-(3-trifluoromethylphenyl)propionate
(e) ethyl 3-(4-dimethylaminophenyl)propionate
(f) ethyl 3-(4-phenoxyphenyl)propionate
(g) ethyl 3-(4-(4-chlorophenoxy)phenyl)propionate
(h) ethyl 3-(4-(4-methoxyphenoxy)phenyl)propionate
(i) ethyl 3-(4-biphenylyl)propionate
(j) ethyl 3-(4'-chloro-4-biphenylyl)propionate
(k) ethyl 3-(4'-methoxy-4-biphenylyl)propionate for ethyl 3-(3-pyridyl)propionate in the procedure of Example 5(iv)–(vi) gives the corresponding 2-[2-(3-(dimethylaminomethyl)-benzylthio)ethylamino]-5-(arylmethyl)-4-pyrimidones.

Treatment of the product from (c) with hydrochloric acid gives the 5-(3-hydroxybenzyl)pyrimidone.

EXAMPLE 26

Substitution of the following 3-(heteroaryl)propionates:
(a) ethyl 3-(2-furyl)propionate
(b) ethyl 3-(2-thiazolyl)propionate
(c) ethyl 3-(5-oxazolyl)propionate
(d) ethyl 3-(3-isothiazolyl)propionate
(e) ethyl 3-(2-pyrimidyl)propionate
(f) ethyl 3-(5-pyrimidyl)propionate
(g) ethyl 3-(2-pyrazyl)propionate
(h) ethyl 3-(4-pyridazyl)propionate
(i) ethyl 3-(2-(5-amino-1,3,4-thiadiazolyl)propionate
(j) ethyl 3-(1-isoquinolyl)propionate
(k) ethyl 3-(4-(1,3-dioxolo[4,5-C]-pyridyl)propionate
(l) ethyl 3-(2-benzimidazolyl)propionate
(m) ethyl 3-(2-benzthiazolyl)propionate for ethyl 3-(6-methyl-3-pyridyl)propionate in the procedure of Example 5(iv)–(vi) gives the corresponding 2-[2-(3-(dimethylaminomethyl)-benzylthio]-5-(heteroarylmethyl)-4-pyrimidones.

The starting materials can be prepared as described in Example 24.

EXAMPLE 27

Substitution of 3-[1-(4-methoxybenzyl)imidazol-2-yl]acrylic acid for 3-(6-methyl-3-pyridyl)acrylic acid in the procedure of Example 5 and deprotection of the product with anisole and hydrogen bromide in acetic acid gives 2-[2-(3-(dimethylaminomethyl)-benzylthio)ethylamino]-5-(2-imidazolylmethyl)-4-pyrimidone.

EXAMPLE 28

Reaction of 2-methylthio-5-methyl-4-pyrimidone with one equivalent of 2-(3-(dimethylaminomethyl)benzylthio)ethylamine by boiling under reflux in pyridine for 48 hours gives 2-[2-(3-dimethylaminomethyl)-benzylthio)ethylamino]-5-methyl-4-pyrimidone.

EXAMPLE 29

Substitution of
(a) ethyl octanoate
(b) ethyl 3-cyclohexylpropionate for ethyl 3-(6-methyl-3-pyridyl)propionate in the procedure of Example 5(iv)–(vi) gives
(iv)(a) 5-hexyl-2-thiouracil m.p. 169.5°–172° (from aqueous ethanol)
(b) 5-cyclohexylmethyl-2-thiouracil m.p. 210°–211° (from ethanol)
(v)(a) 5-hexyl-2-methylthio-4-pyrimidone m.p. 116°–117.5° (from aqueous ethanol)
(b) 5-cyclohexylmethyl-2-methylthio-4-pyrimidone m.p. 187°–188° (from acetic acid)
(vi)(a) 2-[2-(3-(dimethylaminomethyl)-benzylthio)ethylamino]-5-hexyl-4-pyrimidone
(b) 2-[2-(3-(dimethylaminomethyl)-benzylthio)ethylamino]-5-cyclohexylmethyl-4-pyrimidone

EXAMPLE 30

Reaction of
(i) 2-(2-fluorobenzylthio)ethylamine
(ii) 2-(2-chlorobenzylthio)ethylamine
(iii) 2-(2-methylbenzylthio)ethylamine
(iv) 2-(4-methoxybenzylthio)ethylamine
(v) 2-(4-nitrobenzylthio)ethylamine
(vi) 2-(2,4-dichlorobenzylthio)ethylamine
(vii) 4-(4-chlorophenyl)butylamine
(viii) 4-(2-aminophenyl)butylamine
(ix) 4-(4-hydroxyphenyl)butylamine
(x) 4-(3,4-dihydroxyphenyl)butylamine with 2-nitroamino-5-(6-methyl-3-pyridylmethyl)-4-pyrimidone by refluxing in ethanol for 24 hours gives:
(a) 2-[2-(2-fluorobenzylthio)ethylamino]-5-(6-methyl-3-pyridylmethyl)-4-pyrimidone
(b) 2-[2-(2-chlorobenzylthio)ethylamino]-5-(6-methyl-3-pyridylmethyl)-4-pyrimidone
(c) 2-[2-(2-methylbenzylthio)ethylamino]-5-(6-methyl-3-pyridylmethyl)-4-pyrimidone
(d) 2-[2-(4-methoxybenzylthio)ethylamino]-5-(6-methyl-3-pyridylmethyl)-4-pyrimidone
(e) 2-[2-(4-nitrobenzylthio)ethylamino]-5-(6-methyl-3-pyridylmethyl)-4-pyrimidone
(f) 2-[2-(2,4-dichlorobenzylthio)ethylamino]-5-(6-methyl-3-pyridylmethyl)-4-pyrimidone
(g) 2-[4-(4-chlorophenyl)butylamino]-5-(6-methyl-3-pyridylmethyl)-4-pyrimidone
(h) 2-[4-(2-aminophenyl)butylamino]-5-(6-methyl-3-pyridylmethyl)-4-pyrimidone
(i) 2-[4-(4-hydroxyphenyl)butylamino]-5-(6-methyl-3-pyridylmethyl)-4-pyrimidone
(j) 2-[4-(3,4-dihydroxyphenyl)butylamino]-5-(6-methyl-3-pyridylmethyl)-4-pyrimidone

EXAMPLE 31

Reaction of
(i) 2-(2-hydroxy-5-methylbenzylthio)ethylamine
(ii) 2-(2-trifluoromethylbenzylthio)ethylamine
(iii) 2-(2-aminobenzylthio)ethylamine
(iv) 2-(2-(methylamino)benzylthio)ethylamine
(v) 2-(2-dimethylaminobenzylthio)ethylamine with 2-nitroamino-5-(6-methyl-3-pyridylmethyl)-4-pyrimidone by refluxing in ethanol for 24 hours gives
(a) 2-[2-(2-hydroxy-5-methylbenzylthio)ethylamino]-5-(6-methyl-3-pyridylmethyl)-4-pyrimidone
(b) 2-[2-(2-trifluoromethylbenzylthio)ethylamino]-5-(6-methyl-3-pyridylmethyl)-4-pyrimidone
(c) 2-[2-(2-aminobenzylthio)ethylamino]-5-(6-methyl-3-pyridylmethyl)-4-pyrimidone
(d) 2-[2-(2-methylaminobenzylthio)ethylamino]-5-(6-methyl-3-pyridylmethyl)-4-pyrimidone
(e) 2-[2-(2-dimethylaminobenzylthio)ethylamino]-5-(6-methyl-3-pyridylmethyl)-4-pyrimidone The starting materials can be prepared by reacting the corresponding benzyl alcohols with cysteamine.

EXAMPLE 32

Reaction of
(i) 2-(2-acetylaminobenzylthio)ethylamine
(ii) 2-(2-cyanobenzylthio)ethylamine with 2-nitroamino-5-(6-methyl-3-pyridylmethyl)-4-pyrimidone by refluxing in ethanol for 24 hours gives
(a) 2-[2-(2-acetylaminobenzylthio)ethylamino]-5-(6-methyl-3-pyridylmethyl)-4-pyrimidone
(b) 2-[2-(2-cyanobenzylthio)ethylamino]-5-(6-methyl-3-pyridylmethyl)-4-pyrimidone The starting materials can be prepared by reacting the corresponding benzyl alcohols with cysteamine. The benzyl alcohols can be prepared by reducing the corresponding benzaldehydes.

EXAMPLE 33

Reaction of 4-(3-(dimethylaminomethyl)phenyl)-butylamine with
(a) 2-nitroamino-5-(3-pyridylmethyl)-4-pyrimidone
(b) 2-nitroamino-5-(6-methyl-3-pyridylmethyl)-4-pyrimidone
(c) 2-nitroamino-5-(5,6-dimethyl-3-pyridylmethyl)-4-pyrimidone
by heating under reflux in pyridine gives:
(a) 2-[4-(3-dimethylaminomethylphenyl)butylamino]-5-(3-pyridylmethyl)-4-pyrimidone
(b) 2-[4-(3-dimethylaminomethylphenyl)butylamino]-5-(6-methyl-3-pyridylmethyl)-4-pyrimidone
(c) 2-[4-(3-dimethylaminomethylphenyl)butylamino)-5-(5,6-dimethyl-3-pyridylmethyl)-4-pyrimidone

EXAMPLE 34

Reaction of 2-(2-methoxybenzylthio)ethylamine with
(a) 2-nitroamino-5-(6-methyl-3-pyridylmethyl)-4-pyrimidone
(b) 2-nitroamino-5-(5,6-dimethyl-3-pyridylmethyl)-4-pyrimidone
by heating under reflux in pyridine gives:
(a) 2-[2-(2-methoxybenzylthio)ethylamino]-5-(6-methyl-3-pyridylmethyl)-4-pyrimidone
(b) 2-[2-(2-methoxybenzylthio)ethylamino]-5-(5,6-dimethyl-3-pyridylmethyl)-4-pyrimidone

PREPARATION OF PHARMACEUTICAL COMPOSITION FOR ORAL ADMINISTRATION

A pharmaceutical composition is prepared containing

|  | % w/w |
|---|---|
| 2-[2-(3-dimethylaminomethyl)benzylthio)-ethylamino)-5-(6-methyl-3-pyridylmethyl)- | 55 |

-continued

| | | % w/w |
|---|---|---|
| A | 4-pyrimidone | |
| | Dibasic calcium phosphate dihydrate | 20 |
| | Approved colouring agent | 0.5 |
| | Polyvinylpyrrolidone | 4.0 |
| | Microcrystalline cellulose | 8.0 |
| B | Maize starch | 8.0 |
| | Sodium starch glycollate | 0.5 |
| | Magnesium stearate | 0.5 | by mixing together the ingredients A (substituting lactose or microcrystalline cellulose for dibasic calcium phosphate dihydrate if desired), adding a concentrated solution of polyvinylpyrrolidone, and granulating, drying and screening the dried granules; adding the ingredients B to the dried granules and compressing the mixture into tablets, containing an amount of product corresponding to 100 mg, 150 mg or 200 mg of the free base.

The other compounds of Structure 1 can be formulated into pharmaceutical compositions in a similar manner, and these compositions are administered to a subject within the dose ranges given above to block histamine $H_2$-receptors.

We claim:

1. A compound of Structure 1

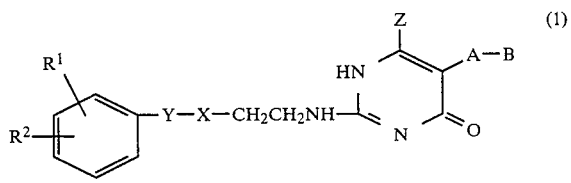

(1)

in which $R^1$ is hydrogen or lower alkoxy; $R^2$ is in the 3-, 4- or 5-position and is lower alkyl substituted by $R^3$, or ethoxy or propoxy ω-substituted by $R^3$ where $R^3$ is amino, lower alkylamino, di(lower alkyl)amino, N-piperidino or N-pyrrolidino; Y is methylene or oxygen and X is methylene or sulphur provided that one or two of the groups X and Y is methylene; Z is hydrogen or lower alkyl; A is $C_1$–$C_5$ alkylene or —$(CH_2)_pW$—$(CH_2)_q$— where W is oxygen or sulphur and p and q are such that their sum is from 1 to 4, and B is 6-methoxy-3-pyridyl, 2-methoxy-4-pyridyl, 6-hydroxy-3-pyridyl or 2-hydroxy-4-pyridyl, in the form of the free base or a pharmaceutically acceptable acid addition salt thereof.

2. A compound of claim 1 in which $R^2$ is lower alkyl substituted by di(lower alkyl)amino.

3. A compound of claim 1 in which $R^2$ is dimethylaminomethyl.

4. A compound of any one of claims 1, 2, or 3 in which Y is methylene.

5. A compound of claim 1 in which $R^2$ is lower alkyl substituted by lower alkylamino, di(lower alkyl)amino or pyrrolidino and $R^1$ is hydrogen or methoxy.

6. A compound of the formula:

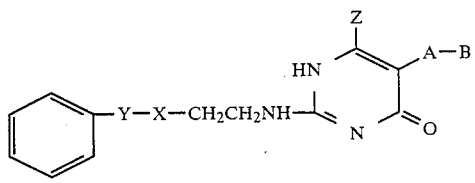

in which Y is methylene or oxygen and X is methylene or sulphur provided that one or two of the groups X and Y is methylene; Z is hydrogen or lower alkyl; A is $C_1$–$C_5$ alkylene or —$(CH_2)_pW$—$(CH_2)_q$— where W is oxygen or sulphur and p and q are such that their sum is from 1 to 4, and B is $C_3$–$C_6$ cycloalkyl, heteroaryl selected from pyridyl, N-oxo-pyridyl, furyl, thienyl, thiazolyl, oxazolyl, isothiazolyl, imidazolyl, pyrimidyl, pyrazyl, pyridazyl, thiadiazolyl, quinolyl, isoquinolyl, 5,6,7,8-tetrahydroquinolyl, benzimidazolyl and benzthiazolyl, said heteroaryl being optionally substituted by one or two lower alkyl or lower alkoxy groups or by one halo, hydroxy or amino group, or B is naphthyl, 6-(2,3-dihydro-1,4-benzodioxinyl), 4- or 5-(1,3-benzodioxolyl) or phenyl optionally substituted with one, two or three lower alkoxy or one or two lower alkyl, halogen, phenyl(lower alkoxy), hydroxy, lower alkoxy-lower alkoxy, trifluoromethyl, di(lower alkyl)amino, phenoxy, halophenoxy, lower alkoxyphenoxy, phenyl, halophenyl or lower alkoxyphenyl groups, in the form of the free base or a pharmaceutically acceptable acid addition salt thereof.

7. A compound of claim 6, said compound being 2-(4-phenylbutylamino)-5-(6-methyl-3-pyridylmethyl)-4-pyrimidone.

8. A pharmaceutical composition having histamine $H_2$-receptor blocking activity comprising in an effective amount to block said receptors a compound of claim 1 and a pharmaceutically acceptable diluent or carrier.

9. A method of blocking histamine $H_2$-receptors which comprises administering to an animal in need thereof in an effective amount to block said receptors a compound of claim 1.

10. A method of blocking histamine $H_2$-receptors which comprises administering to an animal in need thereof in an effective amount to block said receptors a compound of claim 2.

* * * * *